United States Patent
Andree et al.

(10) Patent No.: US 6,432,879 B1
(45) Date of Patent: Aug. 13, 2002

(54) SUBSTITUTED PHENYL URACILS

(75) Inventors: Roland Andree; Mark Wilhelm Drewes, both of Langenfeld (DE); Markus Dollinger, Overland Park, KS (US); Ingo Wetcholowsky, Vinhedo (BR); Randy Allen Myers, Overland Park, KS (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/554,965

(22) PCT Filed: Nov. 17, 1998

(86) PCT No.: PCT/EP98/07342
§ 371 (c)(1),
(2), (4) Date: May 23, 2000

(87) PCT Pub. No.: WO99/28302
PCT Pub. Date: Jun. 10, 1999

(30) Foreign Application Priority Data

Nov. 28, 1997 (DE) .......................... 197 52 748

(51) Int. Cl.$^7$ ................ C07D 239/54; A01N 43/54
(52) U.S. Cl. ............. 504/243; 504/240; 504/236; 544/310; 544/311; 544/312; 544/295; 544/296; 544/284
(58) Field of Search .................. 544/310, 311, 544/312, 295, 296, 284; 504/243, 240, 236

(56) References Cited

U.S. PATENT DOCUMENTS

| | | | |
|---|---|---|---|
| 5,344,812 A | 9/1994 | Theodoridis | 504/243 |
| 5,399,543 A | 3/1995 | Theodoridis | 504/243 |

FOREIGN PATENT DOCUMENTS

| | | |
|---|---|---|
| CA | 2086654 | 7/1993 |
| EP | 0 795 550 | 9/1997 |
| GB | 2034734 | 6/1980 |
| JP | 5-39272 | 2/1993 |
| JP | 5-202031 | 8/1993 |
| WO | 95/17096 | 6/1995 |
| WO | 98/39304 | 9/1998 |
| WO | 98/46592 | 10/1998 |
| WO | 99/01440 | 1/1999 |

OTHER PUBLICATIONS

Justus Liebigs Ann. Der Chemie, 733, (Month Unavailable), 1970, pp. 125–140, Wiegrebe et al, "Synthese des (±)–6–Hydroxy–2.3–dimethoxy–9.11.12.13a.14–Hexahydro–dibenzo[ƒ,h]pyrrolo [1.2–b]isochinolins*".

J. Heterocycl. Chem. 9, Jun. 1972, pp. 513–522, Lutz et al, "Novel 6–(Trifluoromethyl)cytosines and 6–(Trifluoromethyl)uracils".

*Primary Examiner*—John M. Ford
(74) *Attorney, Agent, or Firm*—Joseph C. Gil; Lyndanne M. Whalen; Raymond J. Harmuth

(57) ABSTRACT

The invention relates to novel substituted phenyluracils of the general formula (I)

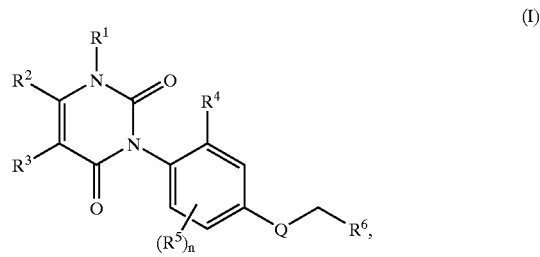

in which the radicals n, Q, $R^1$ to $R^6$ are each as defined in the description, and to processes for this preparation and to their use as herbicides.

7 Claims, No Drawings

SUBSTITUTED PHENYL URACILS

This is a 371 of PCT/EP98/07342, filed Nov. 17, 1998.

The invention relates to novel substituted phenyluracils, to processes for their preparation and to their use as herbicides.

A large number of substituted aryluracils have already been disclosed in the (patent) literature (cf. JP-A-05 202 031, JP-A-05 039 272, U.S. Pat. Nos. 5,344,812, 5,399,543, WO-A-95/17096). However, these compounds have as yet not attained any particular importance.

This invention, accordingly, provides novel substituted phenyluracils of the general formula (I)

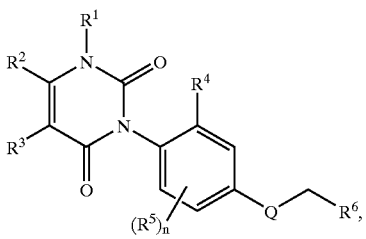

(I)

in which n represents the number 0, 1, 2 or 3,

Q represents O, S. SO, $SO_2$, NH or N(alkyl), $R^1$ represents hydrogen, amino or optionally substituted alkyl, $R^2$ represents carboxyl, cyano, carbamoyl, thiocarbamoyl or represents in each case optionally substituted alkyl or alkoxycarbonyl, $R^3$ represents hydrogen, halogen or optionally substituted alkyl, $R^4$ represents nitro, amino or represents one of the groupings below —NH—CO—$R^7$ or —N(CO—$R^7$)$_2$, $R^5$ represents nitro, amino, hydroxyl, mercapto, carboxyl, cyano, carbamoyl, thiocarbamoyl, sulfo, chlorosulfonyl, aminosulfonyl, halogen, or represents in each case optionally substituted alkyl, alkoxy, alkylthio, alkylsulfinyl, alkylsulfonyl, alkylamino, alkylcarbonyl, alkoxycarbonyl, alkylaminocarbonyl, alkylcarbonylamino, alkoxycarbonylamino, alkylsulfonylamino or bis-alkylsulfonyl-amino, $R^6$ represents optionally substituted aryl or represents optionally substituted heterocyclyl from the group consisting of furyl, tetrahydrofuryl, benzofuryl, dihydrobenzofuryl, dioxolanyl, dioxanyl, benzodioxanyl, pyrrolyl, pyrazolyl, imidazolyl, benzimidazolyl, triazolyl, oxazolyl, isoxazolyl, benzoxazolyl, thiazolyl, isothiazolyl, benzothiazolyl, pyridinyl, quinolinyl, isoquinolinyl, pyrimidinyl, pyrazinyl, pyridazinyl, quinazolinyl, quinoxalinyl, and $R^7$ represents hydrogen or represents in each case optionally substituted alkyl, alkoxy, alkylthio, alkylamino, dialkylamino, alkenyl, alkinyl, cycloalkyl, cycloalkylalkyl, aryl, arylalkyl, heterocyclyl or heterocyclylalkyl.

In the definitions, the hydrocarbon chains, such as alkyl— also in combination with heteroatoms, such as in alkoxy— are in each case straight-chain or branched.

The invention preferably provides substituted phenyluracils of the formula (I), in which n represents the number 0, 1, 2 or 3, Q represents O, S, SO, $SO_2$, NH or N($C_1$–$C_4$-alkyl), $R^1$ represents hydrogen, amino or optionally cyano-, halogen- or $C_1$–$C_4$-alkoxy-substituted alkyl having 1 to 4 carbon atoms, $R^2$ represents carboxyl, cyano, carbamoyl, thiocarbamoyl or represents in each case optionally cyano-, halogen- or $C_1$–$C_4$-alkoxy-substituted alkyl or alkoxycarbonyl having in each case 1 to 4 carbon atoms, $R^3$ represents hydrogen, halogen or optionally halogen-substituted alkyl having 1 to 4 carbon atoms, $R^4$ represents nitro, amino or represents one of the groupings below —NH—CO—$R^7$ or —N(CO—$R^7$)$_2$, $R^5$ represents nitro, amino, hydroxyl, mercapto, carboxyl, cyano, carbamoyl, thiocarbamoyl, sulfo, chlorosulfonyl, aminosulfonyl, halogen, or represents in each case optionally cyano-, halogen- or $C_1$–$C_4$-alkoxy-substituted alkyl, alkoxy, alkylthio, alkylsulfinyl, alkylsulfonyl, alkylamino, alkylcarbonyl, alkoxycarbonyl, alkylaminocarbonyl, alkylcarbonylamino, alkoxycarbonylamino, alkylsulfonylamino or bis-alkylsulfonyl-amino having in each case 1 to 6 carbon atoms in the alkyl groups, $R^6$ represents in each case optionally nitro-, cyano-, carboxyl-, carbamoyl-, thiocarbamoyl-, sulfo-, chlorosulfonyl-, aminosulfonyl-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulfinyl-, $C_1$–$C_4$-halogenoalkylsulfinyl-, $C_1$–$C_4$-alkylsulfonyl-, $C_1$–$C_4$-halogenoalkylsulfonyl- or $C_{1-C4}$-alkoxy-carbonyl-substituted phenyl, naphthyl or heterocyclyl from the group consisting of furyl, tetrahydrofuryl, benzofuryl, dihydrobenzofuryl, dioxolanyl, dioxanyl, benzodioxanyl, pyrrolyl, pyrazolyl, imidazolyl, benzimidazolyl, triazolyl, oxazolyl, isoxazolyl, benzoxazolyl, thiazolyl, isothiazolyl, benzothiazolyl, pyridinyl, quinolinyl, isoquinolinyl, pyrimidinyl, pyrazinyl, pyridazinyl, quinazolinyl, quinoxalinyl, and $R^7$ represents hydrogen, represents in each case optionally cyano-, halogen- or $C_1$–$C_4$-alkoxy-substituted alkyl, alkoxy, alkylthio, alkylamino or dialkylamino having in each case 1 to 6 carbon atoms in the alkyl groups, represents in each case optionally cyano- or halogen-substituted alkenyl or alkinyl having in each case 2 to 6 carbon atoms, represents in each case optionally cyano-, halogen- or $C_1$–$C_4$-alkyl-substituted cycloalkyl or cycloalkylalkyl having in each case 3 to 6 carbon atoms in the cycloalkyl groups and optionally 1 to 4 carbon atoms in the alkyl moiety, or represents in each case optionally nitro-, cyano-, carboxyl-, carbamoyl-, thiocarbamoyl-, sulfo-, chlorosulfonyl-, aminosulfonyl-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulfinyl-, $C_1$–$C_4$-halogenoalkylsulfinyl-, $C_1$–$C_4$-alkylsulfonyl-, $C_1$–$C_4$-halogenoalkyl sulfonyl- or $C_1$–$C_4$-alkoxycarbonyl-substituted phenyl, naphthyl or heterocyclyl from the group consisting of furyl, tetrahydrofuryl, benzofuryl, dihydrobenzofuryl, benzodioxanyl, pyrrolyl, pyrazolyl, imidazolyl, benzimidazolyl, oxazolyl, isoxazolyl, benzoxazolyl, benzothiazolyl, pyridinyl, quinolinyl, isoquinolinyl, pyrimidinyl, pyrazinyl, pyridazinyl, quinazolinyl, quinoxalinyl.

The invention relates in particular to compounds of the formula (I) in which n represents the number 0, 1 or 2, Q represents O, S, SO, SO$_2$, NH or N(CH$_3$), $R^1$ represents hydrogen, amino or in each case optionally cyano-, fluorine-, chlorine-, methoxy- or ethoxy-substituted methyl, ethyl, n- or i-propyl, $R^2$ represents carboxyl, cyano, carbamoyl, thiocarbamoyl or represents in each case optionally cyano-, fluorine-, chlorine-, methoxy- or ethoxy-substituted methyl, ethyl, n- or i-propyl, methoxycarbonyl, ethoxycarbonyl, n- or i-propoxycarbonyl, $R^3$ represents hydrogen, fluorine, chlorine, bromine or represents in each case optionally fluorine- and/or chlorine-substituted methyl, ethyl, n- or i-propyl, $R^4$ represents nitro, amino or represents one of the groupings below —NH—CO—$R^7$ or —N(CO—$R^7$)$_2$, $R^5$ represents nitro, amino, hydroxyl, mercapto, carboxyl, cyano, carbamoyl, thiocarbamoyl, sulfo, chlorosulfonyl, aminosulfonyl, fluorine, chlorine, bromine, or represents in each case optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylsulfinyl, ethylsulfinyl, methylsulfonyl, ethylsulfonyl, methylamino, ethylamino, n- or i-propylamino, acetyl, propionyl, methoxycarbonyl, ethoxycarbonyl, methylaminocarbonyl, ethylaminocarbonyl, acetylamino, propionylamino, methoxycarbonylamino, ethoxycarbonylamino, methylsulfonylamino, ethylsulfonylamino, bis-methylsulfonyl-amino or bis-ethylsulfonyl-amino, $R^6$ represents in each case optionally nitro-, cyano-, carboxyl-, carbamoyl-, thiocarbamoyl-, sulfo-, chlorosulfonyl-, aminosulfonyl-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$alkylthio-, $C_1$–$C_4$-halogenoalkylthio-, $C_1$–$C_4$-alkylsulfinyl-, $C_1$–$C_4$-halogenoalkylsulfinyl-, $C_1$–$C_4$-alkylsulfonyl-, $C_1$–$C_4$-halogenoalkylsulfonyl- or $C_1$–$C_4$-alkoxy-carbonyl-substituted phenyl, naphthyl or heterocyclyl from the group consisting of furyl, tetrahydrofuryl, benzofuryl, dihydrobenzofuryl, dioxolanyl, dioxanyl, benzodioxanyl, pyrrolyl, pyrazolyl, imidazolyl, benzimidazolyl, triazolyl, oxazolyl, isoxazolyl, benzoxazolyl, thiazolyl, isothiazolyl, benzothiazolyl, pyridinyl, quinolinyl, isoquinolinyl, pyrimidinyl, pyrazinyl, pyridazinyl, quinazolinyl, quinoxalinyl, and $R^7$ represents hydrogen, represents in each case optionally cyano-, halogen- or $C_1$–$C_4$-alkoxy-substituted alkyl, alkoxy, alkylthio, alkylamino or dialkylamino having in each case 1 to 6 carbon atoms in the alkyl groups, represents in each case optionally cyano- or halogen-substituted alkenyl or alkinyl having in each case 2 to 6 carbon atoms, represents in each case optionally cyano-, halogen- or $C_1$–$C_4$-alkyl-substituted cycloalkyl or cycloalkylalkyl having in each case 3 to 6 carbon atoms in the cycloalkyl groups and optionally 1 to 4 carbon atoms in the alkyl moiety, or represents in each case optionally nitro-, cyano-, carboxyl-, carbamoyl-, thiocarbamoyl-, sulfo-, chlorosulfonyl-, aminosulfonyl-, halogen-, $C_1$–$C_4$-alkyl-, $C_1$–$C_4$-haloogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulfinyl-, $C_1$–$C_4$-halogenoalkylsulfinyl-, $C_1$–$C_4$-alkylsulfonyl-, $C_1$–$C_4$-halogenoalkylsulfonyl- or $C_1$–$C_4$-alkoxy-carbonyl-substituted phenyl, naphthyl or heterocyclyl from the group consisting of furyl, tetrahydrofuryl, benzofuryl, dihydrobenzofuryl, benzodioxanyl, pyrrolyl, pyrazolyl, imidazolyl, benzimidazolyl, oxazolyl, isoxazolyl, benzoxazolyl, benzothiazolyl, pyridinyl, quinolinyl, isoquinolinyl, pyrimidinyl, pyrazinyl, pyridazinyl, quinazolinyl, quinoxalinyl.

Very particular preference is given to compounds of the formula (I)

in which n represents the number 0,

Q represents O, $R^1$ represents hydrogen or even more preferably methyl, $R^2$ represents trifluoromethyl, $R^3$ represents hydrogen, $R^4$ represents a group as listed in Table 1 and $R^6$ represents phenyl which is substituted in the para-position by chlorine.

The abovementioned general or preferred radical definitions apply both to the end products of the formula (I) and, correspondingly, to the starting materials or intermediates required in each case for the preparation. These radical definitions can be combined with one another at will, i.e. including combinations between the given preferred ranges.

Examples of compounds of the general formula (I) according to the invention are listed in the groups below.

Group 1

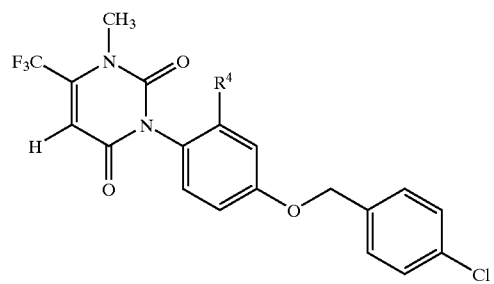

$R^4$ has the meanings given in the list below:

NO$_2$, NH$_2$, —NH—CO—CH$_3$, —NH—CO—C$_2$H$_5$, —NH—CO—C$_3$H$_7$-n, —NH—CO—C$_3$H$_7$-i, —NH—CO—C$_4$H$_9$-n, —NH—CO—C$_4$H$_9$-i, —NH—CO—C$_4$H$_9$-s, —NH—CO—C$_4$H$_9$-t, —NH—CO—CF$_3$, —NH—CO—CHCl$_2$, —NH—CO—CH$_2$—OCH$_3$, —NH—CO-cyclopropyl, —NH—CO-phenyl, —NH—CO-(3-fluorophenyl), —NH—CO-(4-fluorophenyl), —NH—CO-(3-chlorophenyl), —NH—CO-(4-chlorophenyl), —NH—CO-(3-methylphenyl), —NH—CO-(4-methoxyphenyl), —NH—CO-(3- trifluoromethylphenyl), —NH—CO-(3-trifluoromethylphenyl), —NH—CO-(3-methoxyphenyl), —NH—CO-(4-methoxyphenyl), —NH—CO-(4-trifluoromethoxyphenyl), —NH—CO-(2-furyl), —NH—CO-(3-furyl), —NH—CO-(2-thienyl), —NH—CO-(3-thienyl), —N(CO—CH$_3$)2, —N(CO—C$_2$H$_5$)$_2$, —N(CO—CF$_3$)$_2$.

Group 2

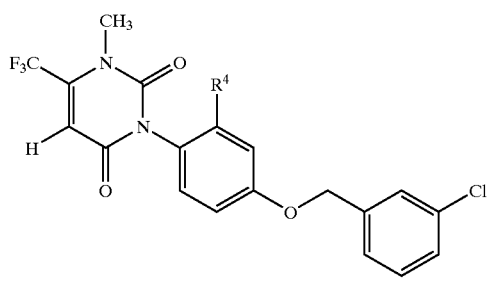

R$^4$ has the meanings given above in Group 1.

Group 3

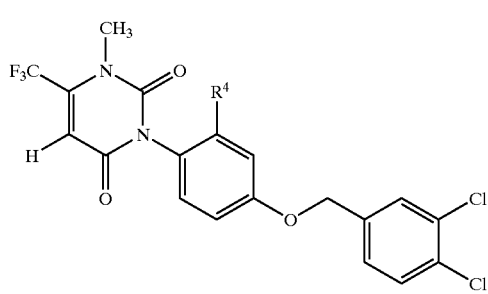

R$^4$ has the meanings given above in Group 1.

Group 4

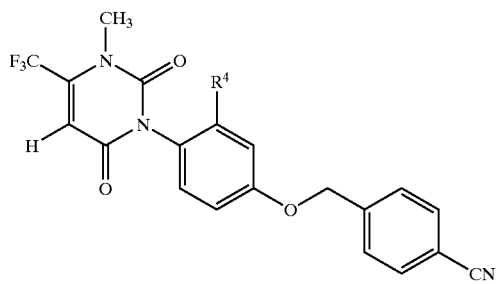

Group 5

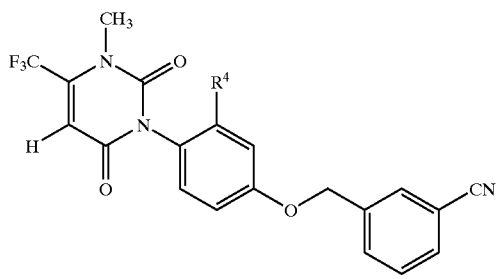

R$^4$ has the meanings given above in Group 1.

Group 6

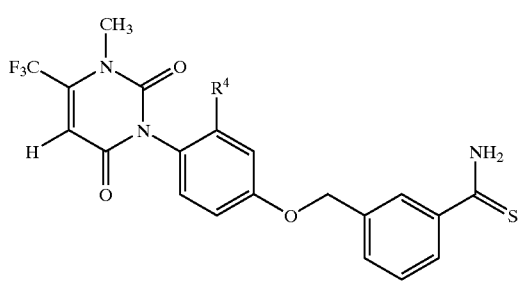

R$^4$ has the meanings given above in Group 1.

Group 7

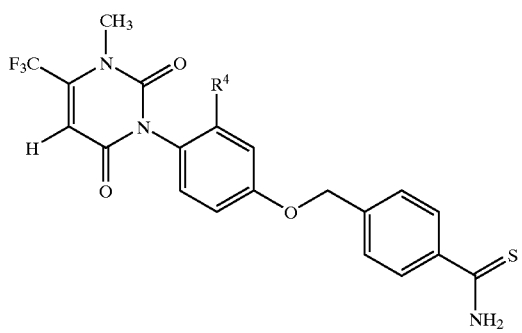

R$^4$ has the meanings given above in Group 1.

Group 8

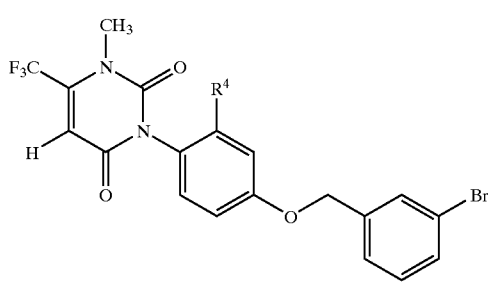

Group 9

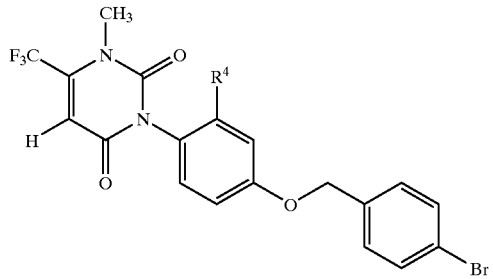

$R^4$ has the meanings given above in Group 1.

Group 10

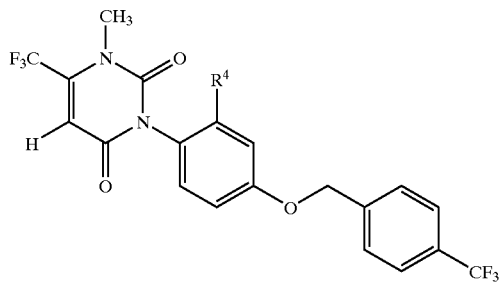

$R^4$ has the meanings given above in Group 1.

Group 11

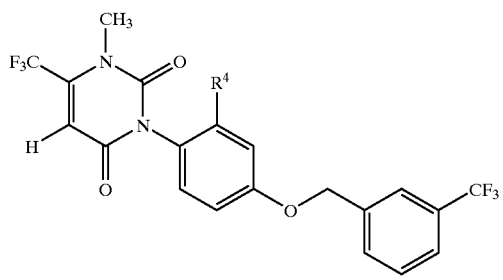

$R^4$ has the meanings given above in Group 1.

Group 12

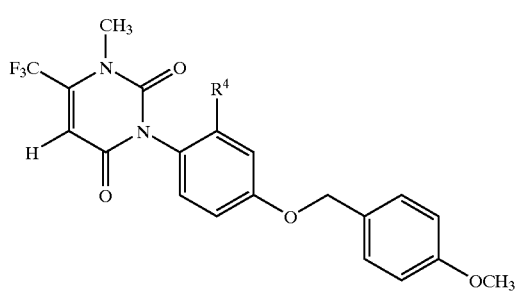

$R^4$ has the meanings given above in Group 1.

Group 13

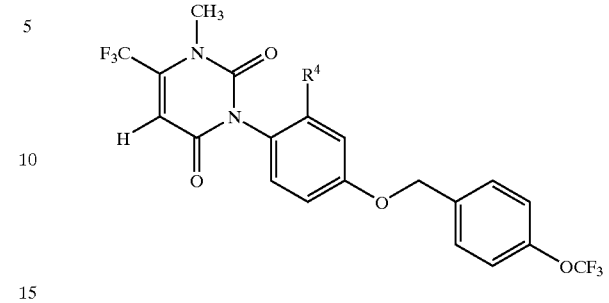

$R^4$ has the meanings given above in Group 1.

Group 14

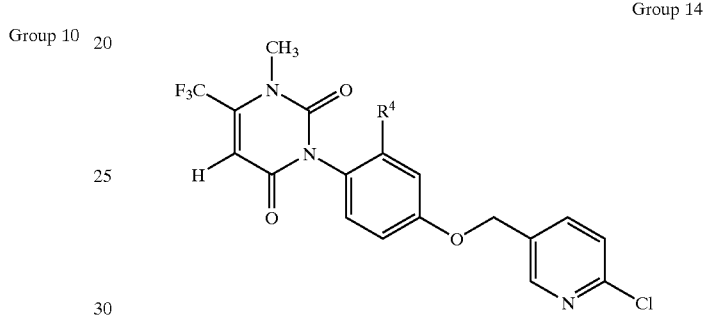

$R^4$ has the meanings given above in Group 1.

Group 15

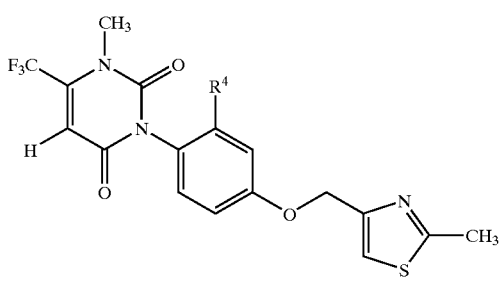

$R^4$ has the meanings given above in Group 1.

Group 16

$R^4$ has the meanings given above in Group 1.

The novel substituted phenyluracils of the general formula (I) have strong and selective herbicidal activity.

The novel substituted phenyluracils of the general formula (I) are obtained when (a) aminoalkenoic esters of the general formula (II)

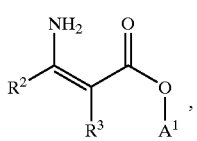
(II)

in which
R² and R³ are each as defined above and
A¹ represents alkyl, aryl or arylalkyl,
are reacted with substituted phenylurethanes (phenylcarbamates) of the general formula (III)

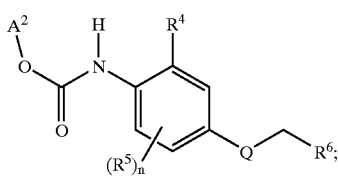
(III)

in which
n, Q, R⁴, R⁵ and R⁶ are each as defined above and
A² represents alkyl, aryl or arylalkyl,
if appropriate in the presence of a reaction auxiliary and if appropriate in the presence of a diluent, or when (b) substituted phenyluracils of the general formula (Ia),

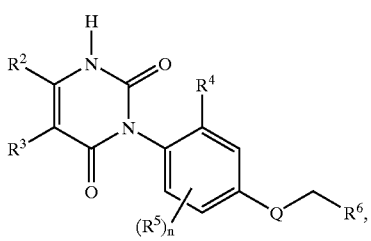
(Ia)

in which
n, Q, R², R³, R⁴, R⁵ and R⁶ are each as defined above,
are reacted with 1-aminooxy-2,4-dinitro-benzene or with alkylating agents of the general formula (IV)

X¹—A³ (IV)

in which
A³ represents optionally substituted alkyl and
X¹ represents halogen or the grouping —O—SO₂—O—A³,
if appropriate in the presence of a reaction auxiliary and if appropriate in the presence of a diluent, or when (c) substituted phenyluracils of the general formula (Ib),

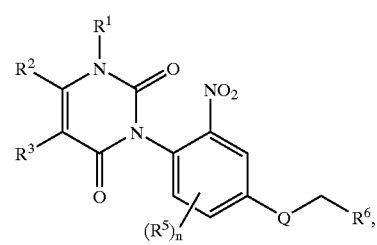
(Ib)

in which
n, Q, R¹, R², R³, R⁵ and R⁶ are each as defined above,
are reacted with hydrogenating agents, if appropriate in the presence of reaction auxiliaries and if appropriate in the presence of diluents, or when (d) substituted phenyluracils of the general formula (Ic),

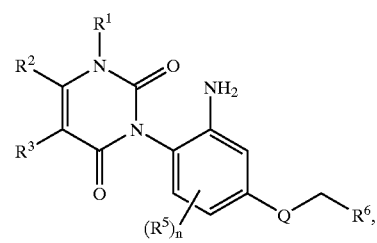
(Ic)

in which
n, Q, R¹, R², R³, R⁵ and R⁶ are each as defined above,
are reacted with acylating agents of the general formula (V)

X²—CO—R⁷ (V)

in which
R⁷ is as defined above and
X² represents halogen or the grouping —O—CO—R⁷,
if appropriate in the presence of reaction auxiliaries and if appropriate in the presence of diluents.

Using, for example, methyl 3-amino-2,4,4,4-tetrafluoro-crotonate and O-methyl N[4-(2-chloro-phenylmethoxy)-2-nitro-phenyl]-carbamate as starting materials, the course of the reaction in the process (a) according to the invention can be illustrated by the following formula scheme:

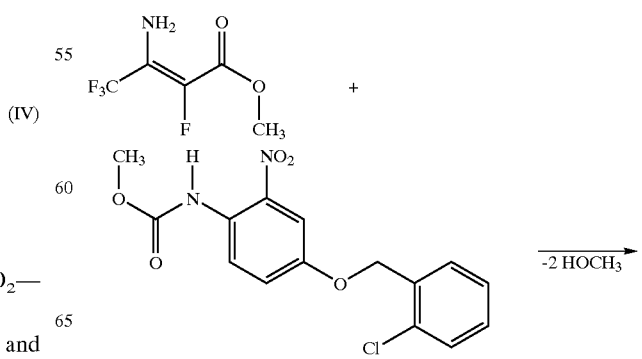

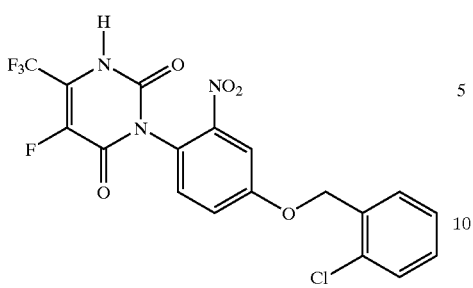

Using, for example, 1-[4-(3-methyl-phenylmethoxy)-2-nitro-phenyl]-5-chloro-4chlorodifluoromethyl-3,6-dihydro-2,6-dioxo-1(2H)-pyrimidine and ethyl bromide as starting materials, the course of the reaction in the process (b) according to the invention can be illustrated by the following formula scheme:

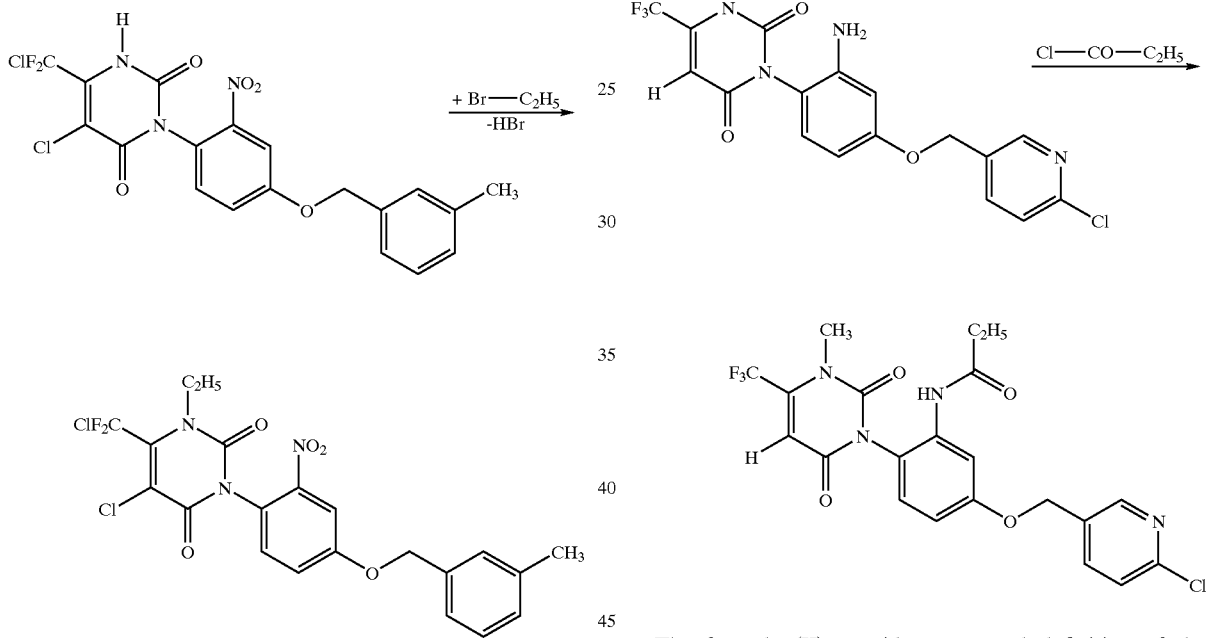

Using, for example, 1-[2-nitro-4-(2-trifluoromethyl-phenylmethoxy)]-3,5-dimethyl-4-trifluoromethyl-3,6-dihydro-2,6-dioxo-1(2H)-pyrimidine and hydrogen in the presence of a catalyst, such as, for example, platinum or palladium, as starting materials, the course of the reaction in the process (c) according to the invention can be illustrated by the following formula scheme:

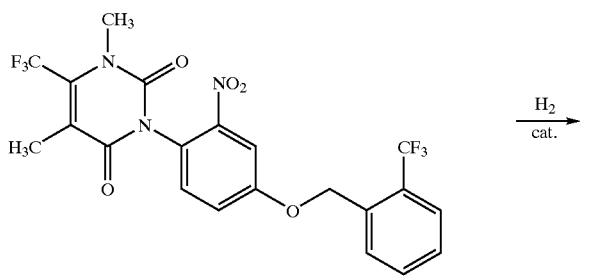

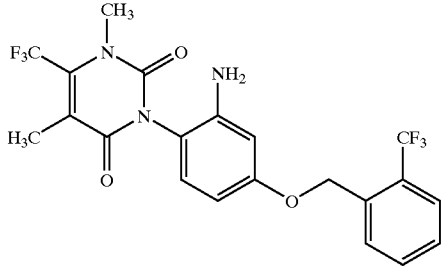

Using, for example, 1-[2-amino-4-(2-chloro-pyridin-5-ylmethoxy)]-3-methyl-4-trifluoromethyl-3,6-dihydro-2,6-dioxo-1(2H)-pyrimidine and propionoyl chloride as starting materials, the course of the reaction in the process (d) according to the invention can be illustrated by the following formula scheme:

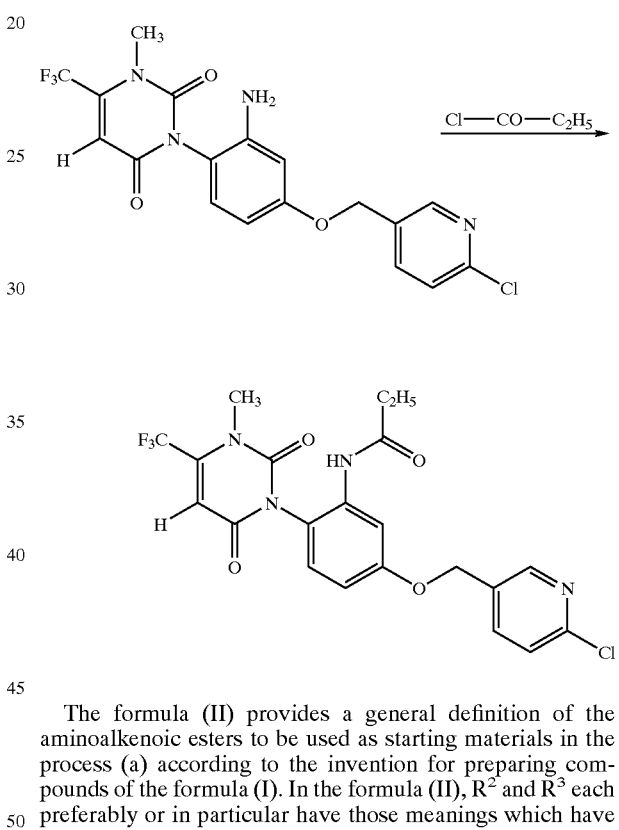

The formula (II) provides a general definition of the aminoalkenoic esters to be used as starting materials in the process (a) according to the invention for preparing compounds of the formula (I). In the formula (II), $R^2$ and $R^3$ each preferably or in particular have those meanings which have already been mentioned above, in connection with the description of the compounds of the formula (I) according to the invention, as being preferred or as being particularly preferred for $R^2$ and $R^3$; $A^1$ preferably represents $C_1$–$C_4$-alkyl, phenyl or benzyl, in particular methyl or ethyl.

The starting materials of the general formula (II) are known and/or can be prepared by known processes (cf. J. Heterocycl. Chem. 9 (1972), 513–522).

The formula (III) provides a general definition of the substituted phenylurethanes further to be used as starting materials in the process (a) according to the invention. In the formula (III), n, Q, $R^4$, $R^5$ and $R^6$ each preferably or in particular have those meanings which have already been mentioned above, in connection with the description of the compounds of the formula (I) according to the invention, as being preferred or as being particularly preferred for n, Q, $R^4$, $R^5$ and $R^6$; $A^2$ preferably represents $C_1$–$C_4$-alkyl, phenyl or benzyl, in particular methyl or ethyl.

The starting materials of the general formula (III) have hitherto not been disclosed in the literature; as novel substances, they also form part of the subject-matter of the present application.

The substituted phenylurethanes (phenylcarbamates) of the general formula (III) are obtained when substituted phenylamines of the general formula (VI)

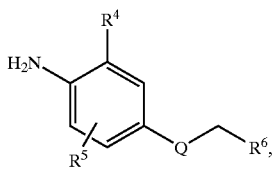

(VI)

in which n, Q, $R^4$, $R^5$ and $R^6$ are each as defined above, are reacted with chloroformic esters of the general formula (VII)

(VII)

in which $A^2$ is as defined above, if appropriate in the presence of an acid acceptor, such as, for example, pyridine, and if appropriate in the presence of a diluent, such as, for example, methylene chloride, at temperatures between 0° C. and 100° C. (cf. the Preparation Examples).

The substituted phenylamines of the general formula (VI) required as intermediates are known and/or can be prepared by processes known per se (cf. Justus Liebigs Ann. Chem. 733 (1970), 125–140; DE-A-28 42 186; Preparation Examples).

The formula (Ia) provides a general definition of the substituted phenyluracils to be used as starting materials in the process (b) according to the invention for preparing compounds of the formula (I). In the formula (Ia), n, Q, $R^2$, $R^3$, $R^4$, $R^5$ and $R^6$ each preferably or in particular have those meanings which have already been mentioned above, in connection with the description of the compounds of the formula (I) according to the invention, as being preferred or as being particularly preferred for n, Q, $R^2$, $R^3$, $R^4$, $R^5$ and $R^6$.

As novel substances, the starting materials of the general formula (Ia) for process (b) also form part of the subject-matter of the present application; they can be prepared by the process (a) according to the invention.

The formula (IV) provides a general definition of the alkylating agents further to be used as starting materials in the process (b) according to the invention. In the formula (IV), $A^3$ preferably represents optionally cyano-, halogen- or $C_1$-$C_4$-alkoxy-substituted alkyl having 1 to 4 carbon atoms and $X^1$ preferably represents chlorine, bromine, iodine, methylsulfonyloxy or ethylsulfonyloxy; in particular, $A^3$ represents in each case optionally cyano-, fluorine-, chlorine-, methoxy- or ethoxy-substituted methyl, ethyl, n- or i-propyl and $X^1$ represents chlorine, bromine, iodine, methyl-sulfonyloxy or ethylsulfonyloxy.

The starting materials of the formula (IV) are known organic chemicals for synthesis.

The formula (Ib) provides a general definition of the substituted phenyluracils to be used as starting materials in the process (c) according to the invention for preparing compounds of the formula (I). In the formula (Ib), n, Q, $R^1$, $R^2$, $R^3$, $R^5$ and $R^6$ each preferably or in particular have those meanings which have already been mentioned above, in connection with the description of the compounds of the formula (I) according to the invention, as being preferred or as being particularly preferred for n, Q, $R^1$, $R^2$, $R^3$, $R^5$ and $R^6$.

As novel substances, the starting materials of the general formula. (Ib) for process (c) also form part of the subject-matter of the present application; they can be prepared by the processes (a) or (b) according to the invention.

The formula (Ic) provides a general definition of the substituted phenyluracils to be used as starting materials in the process (d) according to the invention for preparing compounds of the formula (I). In the formula (Ic), n, Q, $R^1$, $R^2$, $R^3$, $R^5$ and $R^6$ each preferably or in particular have those meanings which have already been mentioned above, in connection with the description of the compounds of the formula (I) according to the invention, as being preferred or as being particularly preferred for n, Q, $R^1$, $R^2$, $R^3$, $R^5$ and $R^6$.

As novel substances, the starting materials of the general formula (Ic) for process (d) also form part of the subject-matter of the present application; they can be prepared by the processes (a), (b) or (c) according to the invention.

The formula (V) provides a general definition of the acylating agents further to be used as starting materials in the process (d) according to the invention. In the formula (V), $R^7$ preferably or in particular has that meaning which has already been mentioned above, in connection with the description of the compounds of the formula (I) according to the invention, as being preferred or as being particularly preferred for $R^7$; $X^2$ preferably represents fluorine, chlorine or bromine, in particular chlorine.

The starting materials of the general formula (V) are known organic compounds for synthesis.

The processes according to the invention for preparing the compounds of the general formula (I) are preferably carried out using diluents. Suitable diluents for carrying out the processes (a) to (d) according to the invention are, in addition to [lacuna], especially, inert organic solvents. These include, in particular, aliphatic, alicyclic or aromatic, optionally halogenated, hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether, or ethylene glycol diethyl ether; ketones, such as acetone, butanone or methyl isobutyl ketone; nitrites, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate, sulfoxides, such as dimethyl sulfoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

Suitable reaction auxiliaries for the processes (a) (b) and (d) according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, -n- or -i-propoxide, n-, -i-,-s- or -t-butoxide or potassium methoxide, ethoxide, n- or i-propoxide, n-, -i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diaza-bicyclo[2.2.2]-octane (DABCO), 1,5-diazabicyclo[4.3.0]-non-5-ene (DBN), or 1,8-diazabicyclo[5.4.0]-undec-7-ene (DBU).

The process (c) according to the invention is carried out using a hydrogenating agent. To this end, it is possible to use the customary hydrogenating agents suitable for reducing nitro compounds. These include, for example, hydrogen, hydrazine (hydrate), metals, such as, for example, iron, in the presence of an acid, such as, for example, hydrochloric acid, sulfuric acid or acetic acid, sulfides, such as, for example, sodium sulfide, and hydride complexes, such as, for example, sodium borohydride.

Suitable reaction auxiliaries, in particular when the hydrogenating agent used is hydrogen or hydrazine (hydrate), are metals, such as platinum, palladium, iron, cobalt, nickel, and, if appropriate, additional supports, such as carbon or kieselguhr.

When carrying out the processes (a) to (d) according to the invention, the reaction temperatures can be varied within a relative wide range. In general, the processes are carried out at temperatures between 0° C. and 200° C., preferably between 10° C. and 150° C.

The processes according to the invention are generally carried out under atmospheric pressure. However, it is also possible to carry out the processes according to the invention under elevated or reduced pressure, in general between 0.1 bar and 100 bar.

To carry out the processes according to the invention, the starting materials are generally employed in approximately equimolar amounts. However, it is also possible to use one of the components in a larger excess. In general, the reaction is carried out in a suitable diluent in the presence of a reaction auxiliary, and the reaction mixture is generally stirred for several hours at the temperature required. Work-up is by customary methods (cf. the Preparation Examples).

The active compounds according to the invention can be used as defoliants, desiccants, haulm killers and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Aniaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

Depending on the concentration, the compounds are suitable for total weed control, for example on industrial terrain and rail tracks, and on paths and areas with or without tree stands. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pastures, and for selective weed control in annual crops.

The compounds of the formula (I) according to the invention are particularly suitable for the selective control of monocotyledonous and dicotyledonous weeds in monocotyledonous crops, both by the pre- and the post-emergence method.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to employ, for example, organic solvents as auxiliary solvents. Liquid solvents which are mainly suitable are: aromatics such as xylene, toluene, or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are: for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam/formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Tackifiers such as carboxymethylcellulose and natural and synthetic polymers in the form of powders, granules or latexes such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, ready mixes or tank mixes being possible.

Possible components for the mixtures are known herbicides, such as, for example, acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazone, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlornitrofen, chlorsulfuron, chlortoluron, cinmethylin, cinosulfuron, clethodim, clodinafop(-propargyl), clomazone, clomeprop, clopyralid, clopyrasulfuron(-methyl), cloransulam(-methyl), cumyluron, cyanazine, cycloate, cyclosulfamuron, cycloxydim, cyhalofop(-butyl), 2,4-D, 2,4-DB, 2,4-DP, desmedipham, di-allate, dicamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymrone, epoprodan, EPTC, esprocarb, ethalfluralin, ethametsulfuron(-methyl), ethofumesate, ethoxyfen, ethoxysulfuron, etobenzanid, fenoxaprop(-P-ethyl), flamprop(-isopropyl), flamprop(-isopropyl-L), flamprop(-methyl), flazasulfuron, fluazifop(-P-butyl), flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate(isopropylammonium), halosafen, haloxyfop(-ethoxyethyl), haloxyfop(-P-methyl), hexazinone, imazamethabenz(-methyl), imazamethapyr, imazamox, imazapyr, imazaquin, imazethapyr, imazosulfuron, ioxynil, isopropalin, isoproturon, isouron, isoxaben, isoxaflutole, isoxapyrifop, lactofen, lenacil, linuron, MCPA, MCPP, mefenacet, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac(-methyl), pyrithiobac(-sodium), quinchlorac, quinmerac, quinoclamine, quizalofop(-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, terbuthylazine, terbutryn, thenylchlor, thiafluamide, thiazopyr, thidiazimin, thifensulfuron(-methyl), thiobencarb, tiocarbazil, tralkoxydim, tri-allate, triasulfuron, tribenuron(-methyl), triclopyr, tridiphane, trifluralin and triflusulfuron.

Mixtures with other known active compounds, such as fungicides, insecticides, acaricides, nematicides, bird repellants, plant nutrients and soil conditioners, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by pouring, spraying, atomizing or spreading.

The active compounds according to the invention can be applied either before or after emergence of the plants. They can also be incorporated into the soil before sowing. The amount of active compound used can vary within a substantial range. It depends essentially on the nature of the desired effect. In general, the application rates are between 1 g and 10 kg of active compound per hectare of soil surface, preferably between 5 g and 5 kg per ha.

The preparation and use of the active compounds according to the invention can be seen from the examples which follow.

Preparation Examples

EXAMPLE 1

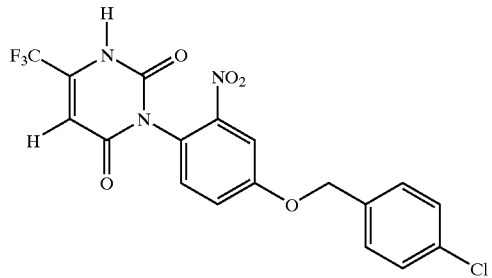

(Process (a))

11.0 g (54 mmol) of ethyl 3-amino-4,4,4-trifluorocrotonate are initially charged in 50 ml of N-methylpyrrolidone and, at room temperature (about 20° C.), admixed successively with stirring with 1.75 g (73 mmol) of sodium hydride and 19.0 g (54 mmol) of O-ethyl N-[4-(4-chloro-phenylmethoxy)-2-nitro-phenyl]-carbamate. The reaction mixture is stirred at 130° C. for 30 minutes. It is then allowed to cool slightly, poured onto ice-water and extracted with ethyl acetate. The aqueous phase is acidified and reextracted with ethyl acetate. The combined organic extracts are washed with water, dried with sodium sulfate and filtered. The filtrate is concentrated under water pump vacuum, the residue is digested with diethyl ether/petroleum ether and the resulting crystalline product is isolated by filtration with suction.

This gives 14.0 g (58.5% of theory) of 1-[4-(4-chloro-phenylmethoxy)-2nitrophenyl]-4-trifluoromethyl-3,6-dihydro-2,6-dioxo-1(2H)-pyrimidin of melting point 237° C.

EXAMPLE 2

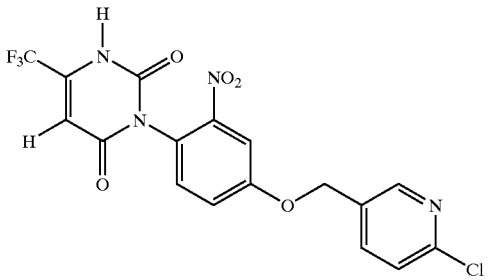

(Process (a))

20.0 g (91 mmol) of ethyl 3-amino-4,4,4-trifluoro-crotonate are initially charged in 80 ml of N-methyl-pyrrolidone and, at room temperature (about 20° C.), admixed successively with stirring with 3.5 g (146 mmol) of sodium hydride and 32.0 g (91 mmol) of O-ethyl N-[4-(2-chloro-pyridin-5-yl-methoxy)-2-nitro-phenyl]carbamate. The reaction mixture is stirred at 130° C. for 45 minutes. It is then allowed to cool slightly, poured onto ice-water and extracted with ethyl acetate. The aqueous phase is acidified and reextracted with ethyl acetate. The combined organic extracts are washed with water, dried with sodium sulfate and filtered. The filtrate is concentrated under water pump vacuum, the residue is digested with diethyl ether/petroleum ether and the resulting crystalline product is isolated by filtration with suction.

This gives 25.6 g (63.5% of theory) of 1-[4-(2-chloro-pyridin-5-yl-methoxy)-2-nitrophenyl]-4-trifluoromethyl-3,6-dihydro-2,6-dioxo-1(2H)-pyrimidine of melting point 209° C.

EXAMPLE 3

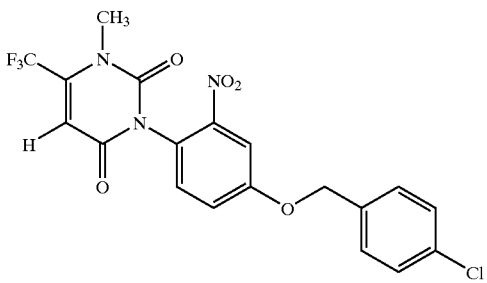

(Process (b))

A mixture of 13.7 g (31 mmol) of 1-[4-(4-chloro-phenylmethoxy)-2-nitro-phenyl]-4-trifluoromethyl-3,6-dihydro-2,6-dioxo-1(2H)-pyrimidine 4.4 g (35 mmol) of di-methyl sulfate, 4.8 g of potassium carbonate and 150 ml of acetone is heated under reflux for 30 minutes and subsequently concentrated under water pump vacuum. The residue is stirred with 1N hydrochloric acid/diethyl ether and the crystalline product is isolated by filtration with suction.

This gives 12.65 g (90% of theory) of 1-[4-(4-chloro-phenylmethoxy)-2-nitrophenyl]-3-methyl-4-trifluoromethyl-3,6-dihydro-2,6-dioxo-1(2H)-pyrimidine of melting point 159° C.

EXAMPLE 4

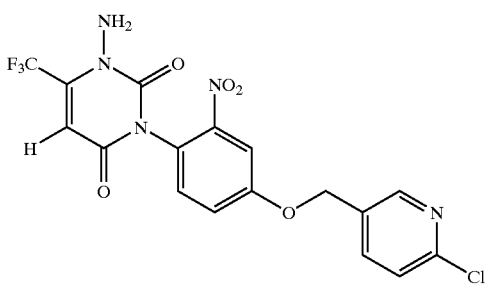

(Process (b))

A mixture of 6.0 g (13.6 mmol) of 1-[4-(2-chloro-pyridin-5-yl-methoxy)-2-nitro-phenyl]4-trifluoromethyl-3,6-dihydro-2,6-dioxo-1(2H)-pyrimidine 4.5 g (22 mmol) of 1-aminooxy-2,4-dinitro-benzene, 2.2 g of sodium bicarbonate and 20 ml of N,N-dimethyl-formamide is stirred at room temperature (about 20° C.) for one week. The mixture is then diluted with 2N aqueous sodium hydroxide solution to about twice its volume and extracted with ethyl acetate. The organic extract is washed with water, dried with sodium sulfate and filtered. The filtrate is concentrated under water pump vacuum, the residue is digested with ethyl acetate/diethyl ether and the resulting crystalline product is isolated by filtration with suction.

This gives 4.8 g (77% of theory) of 3-amino-1-[4-(2-chloro-pyridin-5-yl-methoxy)-2-nitro-phenyl]-4-trifluoromethyl-3,6-dihydro-2,6-dioxo-1(2H)-pyrimidine of melting point 193° C.

EXAMPLE 5

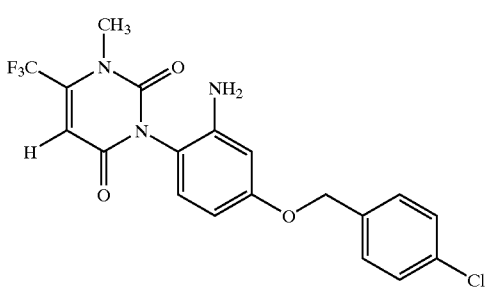

(Process (c))

12.0 g (26.3 mmol) of 1-[4-(4-chloro-phenylmethoxy)-2-nitro-phenyl]-3-methyl-4-trifluoromethyl-3,6-dihydro-2,6-dioxo-1(2H)-pyrimidine are initially charged in 120 ml of acetic acid and 20 ml of water and, at 50° C., mixed a little at a time and with stirring with 7.53 g (134 mmol) of iron (powder). The reaction mixture is then stirred at room temperature (about 20° C.) for another two hours and subsequently concentrated under water pump vacuum. The residue is shaken with water/ethyl acetate and the organic phase is dried with sodium sulfate and filtered. The filtrate is concentrated under water pump vacuum, the residue is digested with diethyl ether/petroleum ether and the resulting crystalline product is isolated by filtration with suction.

This gives 10.5 g (94% of theory) of 1-[2-amino-4-(4-chloro-phenylmethoxy)-phenyl]-3-methyl-4-trifluoromethyl-3,6-dihydro-2,6-dioxo-1(2H)-pyrimidine of melting point 166° C.

EXAMPLE 6

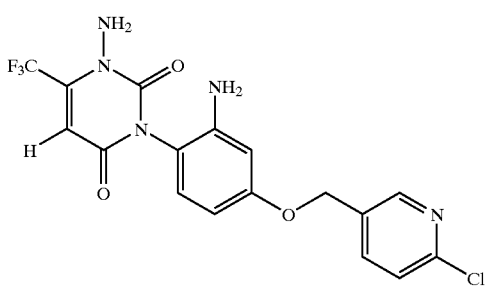

(Process (c))

4.0 g (8.74 mmol) of 1-[4-(2-chloro-pyridin-5-yl-methoxy)-2-nitro-phenyl]-3-methyl-4-trifluoromethyl-3,6-dihydro-2,6-dioxo-1(2H)-pyrimidine are initially charged in 30 ml of acetic acid and 10 ml of water and, at from 50° C. to 80° C., mixed a little at a time and with stirring with 2.67 g (48 mmol) of iron (powder). The reaction mixture is then stirred at room temperature (about 20° C.) for another two hours and subsequently concentrated under water pump vacuum. The residue is shaken with water/ethyl acetate and the organic phase is washed with water, dried with sodium sulfate and filtered. The filtrate is concentrated under water pump vacuum, the residue is digested with diethyl ether/ petroleum ether and the resulting crystalline product is isolated by filtration with suction.

This gives 3.65 g (98% of theory) of 1-[2-amino-4-(2-chloro-pyridin-5-yl-methoxy)phenyl]-3-methyl-4-trifluoromethyl-3,6-dihydro-2,6-dioxo-1(2H)-pyrimidine of melting point 109° C.

EXAMPLE 7

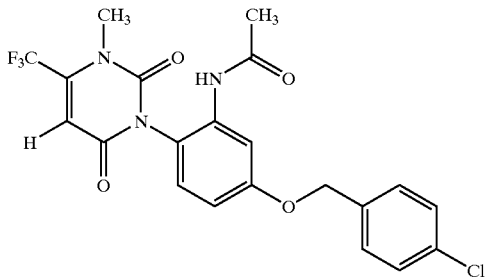

(Process (d))

A mixture of 1.0 g (2.35 mmol) of 1-[2-amino-4-(4-chloro-phenylmethoxy)-phenyl]-3-methyl-4-trifluoromethyl-3,6-dihydro-2,6-dioxo-1(2H)-pyrimidine, 0.24 g (3.1 mmol) of acetyl chloride, 0.30 g of triethylamine and 20 ml of acetonitrile is heated under reflux for two hours and subsequently concentrated under water pump vacuum. The residue is stirred with 2N hydrochloric acid/ethyl acetate/diethyl ether and the resulting crystalline product is isolated by filtration with suction.

This gives 0.60 g (55% of theory) of 1-[2-acetylamino-4-(4-chloro-phenylmethoxy)-phenyl]-3-methyl-4-trifluoromethyl-3,6-dihydro-2,6-dioxo-1(2H)-pyrimidine of melting point 230° C.

EXAMPLE 8

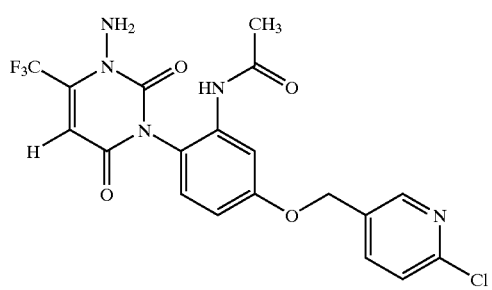

(Process (d))

A mixture of 1.0 g (2.34 mmol) of 1-[2-amino-4-(2-chloro-pyridin-5-yl-methoxy)-phenyl]-3-methyl-4-trifluoromethyl-3,6-dihydro-2,6-dioxo-1(2H)-pyrimidine, 0.23 g (3.0 mmol) of acetyl chloride, 3.0 g of triethylamino and 10 ml of acetonitrile is stirred at 60° C. for 15 minutes and subsequently concentrated under water pump vacuum. The residue is stirred with 2N hydrochloric acid/ethyl acetate/diethyl ether and the resulting crystalline product is isolated by filtration with suction.

This gives 0.50 g (46% of theory) of 1-[2-acetylamino-4-(2-chloro-pyridin-5-ylmethoxy)-phenyl]-3-methyl-4-trifluoromethyl-3,6-dihydro-1(2H)pyrimidine of melting point 228° C.

Analogously to the Preparation Examples 1 to 8 and in accordance with the general description of the preparation processes according to the invention, it is also possible to prepare, for example, the compounds of the formula (I) listed in Table 1 below.

(I)

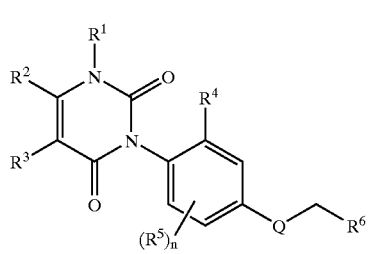

TABLE 1

Examples of the compounds of the formula (I)
- In the compounds of Table 1, n represents in each case the number 0; the meaning of $R^5$ is therefore redundant.

| Ex. No. | Q | $R^1$ | $R^2$ | $R^3$ | $R^4$ | $R^6$ | Melting point (° C.) |
|---|---|---|---|---|---|---|---|
| 9 | O | $CH_3$ | $CF_3$ | H | HN–C(=O)–(2-thienyl), N-methyl | 4-Cl-phenyl | 237 |
| 10 | O | $CH_3$ | $CF_3$ | H | HN–C(=O)–(4-Cl-phenyl), N-methyl | 4-Cl-phenyl | 225 |
| 11 | O | $CH_3$ | $CF_3$ | H | HN–C(=O)–(4-Cl-phenyl), N-methyl | 4-Cl-phenyl | 220 |
| 12 | O | $CH_3$ | $CF_3$ | H | HN–C(=O)–$C(CH_3)_3$, N-methyl | 4-Cl-phenyl | 225 |
| 13 | O | $CH_3$ | $CF_3$ | H | HN–C(=O)–(3-F-phenyl), N-methyl | 4-Cl-phenyl | 228 |
| 14 | O | $CH_3$ | $CF_3$ | H | HN–C(=O)–$C_2H_5$, N-methyl | 4-Cl-phenyl | 228 |
| 15 | O | $CH_3$ | $CF_3$ | H | HN–C(=O)–$C_3H_7$-i, N-methyl | 4-Cl-phenyl | — |
| 16 | O | $CH_3$ | $CF_3$ | H | HN–C(=O)–$C_3H_7$-n, N-methyl | 4-Cl-phenyl | — |
| 17 | O | $CH_3$ | $CF_3$ | H | HN–C(=O)–cyclopropyl, N-methyl | 4-Cl-phenyl | — |
| 18 | O | $CH_3$ | $CF_3$ | H | HN–C(=O)–$CF_3$, N-methyl | 4-Cl-phenyl | 120 |

TABLE 1-continued

Examples of the compounds of the formula (I)
- In the compounds of Table 1, n represents in each case the number 0; the meaning of $R^5$ is therefore redundant.

| Ex. No. | Q | $R^1$ | $R^2$ | $R^3$ | $R^4$ | $R^6$ | Melting point (° C.) |
|---|---|---|---|---|---|---|---|
| 19 | O | $CH_3$ | $CF_3$ | H | –N(CH₃)–C(O)–CH₂–OCH₃ | 4-Cl-phenyl | |
| 20 | O | $CH_3$ | $CF_3$ | H | –N(CH₃)–C(O)–CH₃ | 6-Cl-pyridin-3-yl | 234 |
| 21 | O | $CH_3$ | $CF_3$ | H | –N(CH₃)–C(O)–$C_2H_5$ | 6-Cl-pyridin-3-yl | 233 |
| 22 | O | $CH_3$ | $CF_3$ | H | –N(CH₃)–C(O)–$C_3H_7$-i | 6-Cl-pyridin-3-yl | 190 |
| 23 | O | $CH_3$ | $CF_3$ | H | –N(CH₃)–C(O)–C(CH₃)₃ | 6-Cl-pyridin-3-yl | 204 |
| 24 | O | $CH_3$ | $CF_3$ | H | –N(CH₃)–C(O)–$CF_3$ | 6-Cl-pyridin-3-yl | 137 |
| 25 | O | $CH_3$ | $CF_3$ | H | –N(CH₃)–C(O)–(4-F-phenyl) | 6-Cl-pyridin-3-yl | 188 |
| 26 | O | $CH_3$ | $CF_3$ | H | $NO_2$ | 6-Cl-pyridin-3-yl | 151 |
| 27 | O | $CH_3$ | $CF_3$ | H | $NH_2$ | 6-Cl-pyridin-3-yl | 200 |
| 28 | O | $NH_2$ | $CF_3$ | H | –N(CH₃)–C(O)–(4-F-phenyl) | 6-Cl-pyridin-3-yl | 204 |

TABLE 1-continued

Examples of the compounds of the formula (I)
- In the compounds of Table 1, n represents in each case the number 0; the meaning of $R^5$ is therefore redundant.

| Ex. No. | Q | $R^1$ | $R^2$ | $R^3$ | $R^4$ | $R^6$ | Melting point (° C.) |
|---|---|---|---|---|---|---|---|
| 29 | O | H | $CF_3$ | H | $NO_2$ | 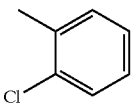 | 189 |
| 30 | O | $CH_3$ | $CF_3$ | H | $NO_2$ | 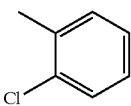 | 119 |
| 31 | O | $CH_3$ | $CF_3$ | H | $NH_2$ | 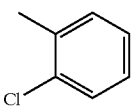 | 171 |
| 32 | O | H | $CF_3$ | H | $NO_2$ | 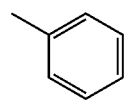 | 228 |
| 33 | O | $CH_3$ | $CF_3$ | H | $NO_2$ | 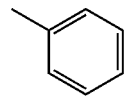 | 162 |
| 34 | O | $CH_3$ | $CF_3$ | H | 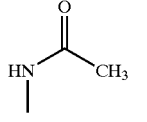 | 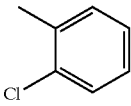 | 207 |
| 35 | O | $CH_3$ | $CF_3$ | H | 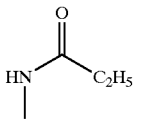 | 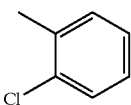 | 158 |
| 36 | O | $CH_3$ | $CF_3$ | H | 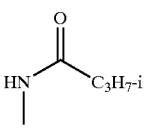 | 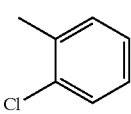 | 100 |
| 37 | O | $CH_3$ | $CF_3$ | H | 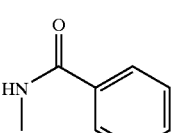 | 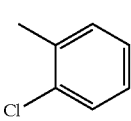 | 209 |
| 38 | O | $CH_3$ | $CF_3$ | H | $NH_2$ | 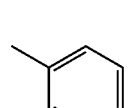 | 165 |
| 39 | O | $CH_3$ | $CF_3$ | H | 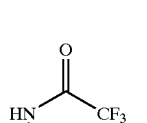 | 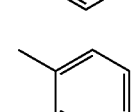 | 119 |

TABLE 1-continued
Examples of the compounds of the formula (I)
- In the compounds of Table 1, n represents in each case the number 0; the meaning of $R^5$ is therefore redundant.
| Ex. No. | Q | $R^1$ | $R^2$ | $R^3$ | $R^4$ | $R^6$ | Melting point (° C.) |
|---|---|---|---|---|---|---|---|
| 40 | O | CH₃ | CF₃ | H | 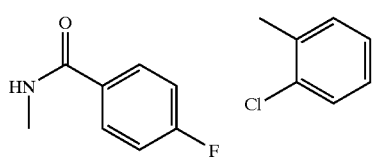 |  | 185 |
| 41 | O | H | CF₃ | H | NO₂ | 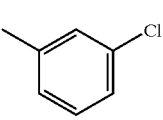 | 215 |
| 42 | O | CH₃ | CF₃ | H | 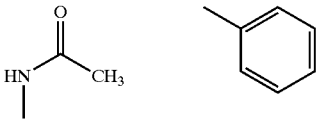 |  | 221 |
| 43 | O | CH₃ | CF₃ | H | 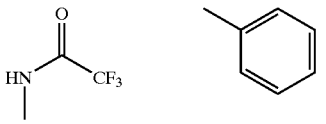 |  | 152 |
| 44 | O | CH₃ | CF₃ | H | 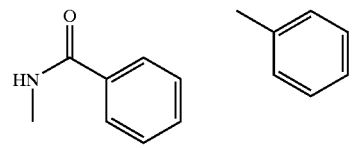 |  | 169 |
| 45 | O | CH₃ | CF₃ | H | NO₂ | 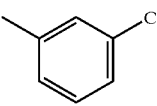 | 170 |
| 46 | O | CH₃ | CF₃ | H | 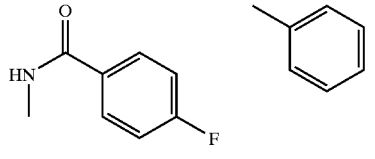 |  | 162 |
| 47 | O | CH₃ | CF₃ | H | 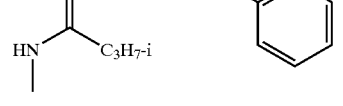 |  | 162 |
| 48 | O | CH₃ | CF₃ | H | 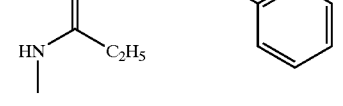 |  | 203 |
| 49 | O | CH₃ | CF₃ | H | NH₂ | 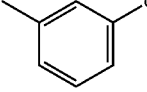 | 178 |

TABLE 1-continued

Examples of the compounds of the formula (I)
- In the compounds of Table 1, n represents in each case the number 0; the meaning of $R^5$ is therefore redundant.

| Ex. No. | Q | $R^1$ | $R^2$ | $R^3$ | $R^4$ | $R^6$ | Melting point (° C.) |
|---|---|---|---|---|---|---|---|
| 50 | O | $CH_3$ | $CF_3$ | H | N-methyl benzamide | 3-Cl-phenyl | 174 |
| 51 | O | $CH_3$ | $CF_3$ | H | N-methyl 4-fluorobenzamide | 3-Cl-phenyl | 175 |
| 52 | O | $CH_3$ | $CF_3$ | H | N-methyl isobutyramide | 3-Cl-phenyl | 167 |
| 53 | O | $CH_3$ | $CF_3$ | H | N-methyl trifluoroacetamide | 3-Cl-phenyl | 115 |
| 54 | O | $CH_3$ | $CF_3$ | H | N-methyl acetamide | 3-Cl-phenyl | 203 |
| 55 | O | $CH_3$ | $CF_3$ | H | N-methyl propionamide | 3-Cl-phenyl | 205 |

Starting Materials of the Formula (III)

Example (III-1)

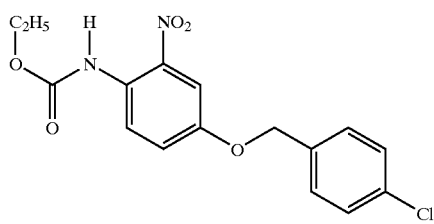

18.1 g (65 mmol) of 1-amino-4-(4-chloro-phenylmethoxy)-2-nitro-benzene are initially charged in 100 ml of acetone and, at 40° C., admixed dropwise with stirring with 16.3 g (mmol) of trichloromethyl chloroformate ("diphosgene") (83 mmol). The reaction mixture is stirred at 40° C. for 20 minutes and then, at room temperature (about 20° C.), added dropwise to 200 ml of ethanol, and this mixture is stirred at room temperature for another 15 minutes and subsequently concentrated under water pump vacuum. The residue is stirred with water/diethyl ether/petroleum ether and the crystalline product is isolated by filtration with suction.

This gives 19.3 g (85% of theory) of O-ethyl N-[4-(4-chloro-phenylmethoxy)-2-nitro-phenyl]-carbamate of melting point 122° C.

Analogously to Example (III-1), it is also possible to prepare, for example, the compounds of the formula (III) listed in Table 2 below.

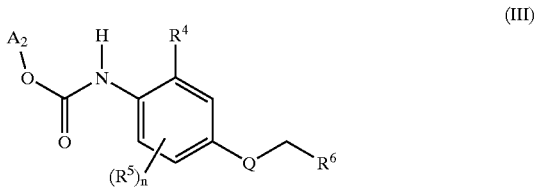

(III)

TABLE 2

Examples of the compounds of the formula (III)
- In the compounds of Table 2, n in each case represents the number 0;
the meaning of $R^5$ is therefore redundant.

| Ex. No. | $A^2$ | Q | $R^4$ | $R^6$ | Physical Data |
|---|---|---|---|---|---|
| III-2 | $C_2H_5$ | O | $NO_2$ | 5-methyl-2-chloropyridin-yl | m.p.: 129° C. |
| III-3 | $C_2H_5$ | O | $NO_2$ | 3,4-dichlorophenyl | |
| III-4 | $C_2H_5$ | O | $NO_2$ | 3-chlorophenyl | m.p.: 99° C. |
| III-5 | $C_2H_5$ | O | $NO_2$ | 4-trifluoromethylphenyl | |
| III-6 | $C_2H_5$ | O | $NO_2$ | 2-bromophenyl | |
| III-7 | $C_2H_5$ | O | $NO_2$ | 4-cyanophenyl | |
| III-8 | $C_2H_5$ | O | $NO_2$ | phenyl | m.p.: 89° C. |
| III-9 | $C_2H_5$ | O | $NO_2$ | 2-chlorophenyl | m.p.: 93° C. |
| III-10 | $CH_3$ | O | $NO_2$ | 3-nitrophenyl | |
| III-11 | $C_2H_5$ | O | $NO_2$ | 4-fluorophenyl | |
| III-12 | $C_2H_5$ | O | $NO_2$ | 2-cyanophenyl | |
| III-13 | $C_2H_5$ | O | $NO_2$ | 3-fluorophenyl | |
| III-14 | $C_2H_5$ | O | $NO_2$ | 4-chloro-3-methylphenyl | |
| III-15 | $C_2H_5$ | O | $NO_2$ | 3-chloro-4-methylphenyl | |
| III-16 | $C_2H_5$ | O | $NO_2$ | 2,4-dichlorophenyl | |
| III-17 | $CH_3$ | O | $NO_2$ | 3,5-dichlorophenyl | |
| III-18 | $CH_3$ | O | $NO_2$ | 2,4-dichlorophenyl | |
| III-19 | $CH_3$ | O | $NO_2$ | 2,3-dichlorophenyl | |

Starting Materials of the Formula (VI)

Example (VI-1)

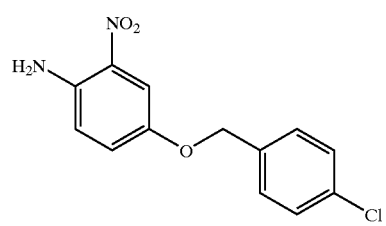

12.0 g (78 mmol) of 4-hydroxy-2-nitro-aniline are initially charged in 50 ml of N-methyl-pyrrolidone and, with stirring, 2.5 g of sodium hydride and 12.0 g (78 mmol) of 4-chloro-benzyl chloride are added successively. The reaction mixture is stirred at room temperature (about 20° C.)

for 20 hours, subsequently admixed with 50 ml of diethyl ether, then poured into ice-water and adjusted to pH=6 with sodium dihydrogen phosphate. The resulting crystalline product is isolated by filtration with suction.

This gives 18.1 g (83.5% of theory) of 1-amino-4-(4-chloro-phenylmethoxy)-2-nitrobenzene.

Analogously to Example (VI-1), it is also possible to prepare, for example, the compounds of the formula (VI) listed in Table 3 below.

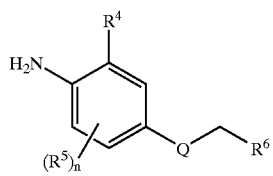

(VI)

TABLE 3

Examples of the compounds of the formula (VI)
- In the compounds of Table 3, n in each case represents the number 0; the meaning of $R^5$ is therefore redundant.

| Ex. No. | Q | $R^4$ | $R^6$ | Physical Data |
|---|---|---|---|---|
| VI-2 | O | $NO_2$ | 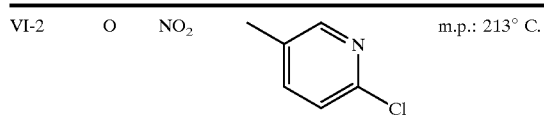 | m.p.: 213° C. |
| VI-3 | O | $NO_2$ | 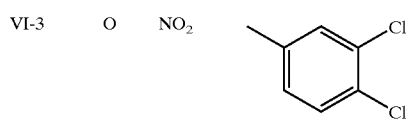 | |
| VI-4 | O | $NO_2$ | 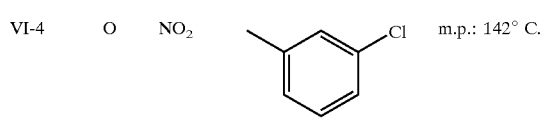 | m.p.: 142° C. |
| VI-5 | O | $NO_2$ | 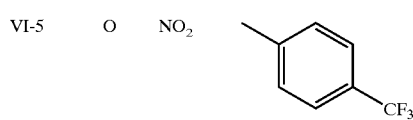 | |
| VI-6 | O | $NO_2$ | 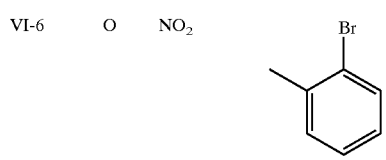 | |
| VI-7 | O | $NO_2$ | 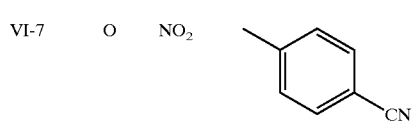 | |
| VI-8 | O | $NO_2$ | 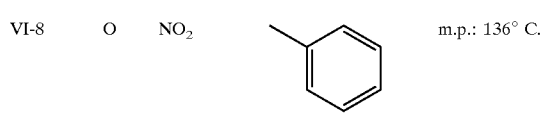 | m.p.: 136° C. |

TABLE 3-continued

Examples of the compounds of the formula (VI)
- In the compounds of Table 3, n in each case represents the number 0; the meaning of $R^5$ is therefore redundant.

| Ex. No. | Q | $R^4$ | $R^6$ | Physical Data |
|---|---|---|---|---|
| VI-9 | O | $NO_2$ | 2-Cl-phenyl | |
| VI-10 | O | $NO_2$ | 3-$NO_2$-phenyl | |
| VI-11 | O | $NO_2$ | 4-F-phenyl | |
| VI-12 | O | $NO_2$ | 2-CN-phenyl | |
| VI-13 | O | $NO_2$ | 3-F-phenyl | |
| VI-14 | O | $NO_2$ | 2-$CH_3$-4-Cl-phenyl | |
| VI-15 | O | $NO_2$ | 2-Cl-4-$CH_3$-phenyl | |
| VI-16 | O | $NO_2$ | 2,4-di-Cl-phenyl | |
| VI-17 | O | $NO_2$ | 3,5-di-Cl-phenyl | |
| VI-18 | O | $NO_2$ | 2,4-di-Cl-phenyl | |

TABLE 3-continued

Examples of the compounds of the formula (VI)
- In the compounds of Table 3, n in each case represents the number 0; the meaning of $R^5$ is therefore redundant.

| Ex. No. | Q | $R^4$ | $R^6$ | Physical Data |
|---|---|---|---|---|
| VI-19 | O | $NO_2$ | 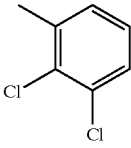 | |

Use Examples

Example A

Pre-emergence Test

Solvent: 5 parts by weight of acetone
Emulsifier: 1 part by weight of alkylaryl polyglycol ether To produce a suitable preparation of active compounds, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compounds such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)
100%=total destruction

In this test, for example, the compounds of Preparation Examples 3, 5 and 7 exhibit strong action against weeds, and some are tolerated well by crop plants, such as, for example, maize.

Example B

Post-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants of a height of 5–15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)
100%=total destruction

In this test, for example, the compounds of preparation examples 5, 7, 9, 10, 11 and 13 exhibit strong activity against weeds, and some are tolerated well by crop plants, such as, for example, maize and wheat.

What is claimed is:

1. A phenyluracil compound of the formula (I),

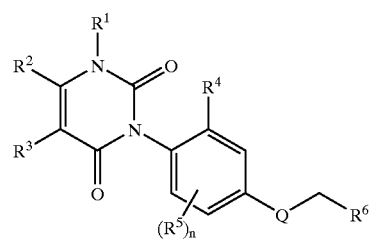

(I)

in which
n represents the number 0, 1, 2 or 3,
Q represents O, S, SO, $SO_2$, NH or N($C_1$–$C_4$-alkyl),
$R^1$ represents hydrogen, amino or optionally cyano-, halogen- or $C_1$–$C_4$alkoxy-substituted alkyl having 1 to 4 carbon atoms,
$R^2$ represents carboxyl, cyano, carbamoyl, thiocarbamoyl or represents in each case optionally cyano-, halogen- or $C_1$–$C_4$-alkoxy-substituted alkyl or alkoxycarbonyl having in each case 1 to 4 carbon atoms,
$R^3$ represents hydrogen, halogen or optionally halogen-substituted alkyl having 1 to 4 carbon atoms,
$R^4$ represents amino or represents one of the groupings below —NH—CO—$R^7$ or —N(CO—$R^7$)$_2$,
$R^5$ represents nitro, amino, hydroxyl, mercapto, carboxyl, cyano, carbamoyl, thiocarbamoyl, sulfo, chlorosulfonyl, aminosulfonyl, halogen, or represents in each case optionally cyano-, halogen- or $C_1$–$C_4$-alkoxy-substituted alkyl, alkoxy, alkylthio, alkylsulfinyl, alkylsulfonyl, alkylamino, alkylcarbonyl, alkoxycarbonyl, alkylaminocarbonyl, alkylcarbonylamino, alkoxycarbonylamino, alkylsulfonylamino or bis-alkylsulfonyl-amino having in each case 1 to 6 carbon atoms in the alkyl groups,
$R^6$ represents in each case optionally nitro-, cyano-, carboxyl-, carbamoyl-, thiocarbamoyl-, sulfo-, chlorosulfonyl-, aminosulfonyl-, halogen-, $C_1$–$C_4$-alkyl-, $C_1$–$C_4$-halogenoalkyl-, $C_1$–$C_4$-alkoxy-, $C_1$–$C_4$halogenoalkoxy-, $C_1$–$C_4$-alkylthio-, $C_1$–$C_4$-halogenoalkylthio-, $C_1$–$C_4$alkylsulfinyl-, $C_1$–$C_4$-halogenoalkylsulfinyl-, $C_1$–$C_4$-alkylsulfonyl-, $C_1$–$C_4$-halogenoalkylsulfonyl- or $C_1$–$C_4$-alkoxy-carbonyl-substituted phenyl, naphthyl or heterocyclyl selected from the group consisting of furyl, tetrahydrofuryl, benzofuryl, dihydrobenzofuryl, dioxolanyl, dioxanyl, benzodioxanyl, pyrrolyl, pyrazolyl, imidazolyl, benzimidazolyl, triazolyl, oxazolyl, isoxazolyl, benzoxazolyl, thiazolyl, isothiazolyl, benzothiazolyl, pyridinyl, quinolinyl, isoquinolinyl, pyrimidinyl, pyrazinyl, pyridazinyl, quinazolinyl, quinoxalinyl, and
$R^7$ represents hydrogen, represents in each case optionally cyano-, halogen- or $C_1$–$C_4$-alkoxy-substituted alkyl, alkoxy, alkylthio, alkylamino or dialkylamino having in each case 1 to 6 carbon atoms in the alkyl groups, represents in each case optionally cyano- or halogen-substituted alkenyl or alkinyl having in each case 2 to 6 carbon atoms, represents in each case optionally cyano-, halogen- or $C_1$–$C_4$-alkyl-substituted cycloalkyl or cycloalkylalkyl having in each case 3 to 6 carbon atoms in the cycloalkyl groups and optionally 1 to 4 carbon atoms in the alkyl moiety, or represents in each case optionally nitro-, cyano-, carboxyl-, carbamoyl-, thiocarbamoyl-, sulfo-, chlorosulfonyl-, aminosulfonyl-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulfinyl-, $C_1$–$C_4$-halogenoalkylsulfinyl-, $C_1$–$C_4$alkylsulfonyl-, $C_1$–$C_4$-halogenoalkylsulfonyl- or $C_1$–$C_4$-alkoxy-carbonyl-substituted phenyl, naphthyl or heterocyclyl selected from the group consisting of furyl, tetrahydrofuryl, benzofuryl, dihydrobenzofuryl, benzodioxanyl, pyrrolyl, pyrazolyl, imidazolyl, benzimidazolyl, oxazolyl, isoxazolyl, benzoxazolyl, benzothiazolyl, pyridinyl, quinolinyl, isoquinolinyl, pyrimidinyl, pyrazinyl, pyridazinyl, quinazolinyl, quinoxalinyl.

2. A phenyluracil compound of the formula (I) according to claim 1, in which n represents the number 0, 1 or 2, Q represents O, S, SO, $SO_2$, NH or $N(CH_3)$, $R^1$ represents hydrogen, amino or in each case optionally cyano-, fluorine-, chlorine-, methoxy- or ethoxy-substituted methyl, ethyl, n- or i-propyl, $R^2$ represents carboxyl, cyano, carbamoyl, thiocarbamoyl or represents in each case optionally cyano-, fluorine-, chlorine-, methoxy- or ethoxy-substituted methyl, ethyl, n- or i-propyl, methoxycarbonyl, ethoxycarbonyl, n- or i-propoxycarbonyl, $R^3$ represents hydrogen, fluorine, chlorine, bromine or represents in each case optionally fluorine- and/or chlorine-substituted methyl, ethyl, n- or i-propyl, $R^4$ represents amino or represents one of the groupings below —NH—CO—$R^7$ or —N(CO—$R^7$)$_2$, $R^5$ represents nitro, amino, hydroxyl, mercapto, carboxyl, cyano, carbamoyl, thiocarbamoyl, sulfo, chlorosulfonyl, aminosulfonyl, fluorine, chlorine, bromine, or represents in each case optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylsulfinyl, ethylsulfinyl, methylsulfonyl, ethylsulfonyl, methylamino, ethylamino, n- or i-propylamino, acetyl, propionyl, methoxycarbonyl, ethoxycarbonyl, methylaminocarbonyl, ethylaminocarbonyl, acetylamino, propionylamino, methoxycarbonylamino, ethoxycarbonylamino, methylsulfonylamino, ethylsulfonylamino, bis-methylsulfonyl-amino or bis-ethylsulfonyl-amino, $R^6$ represents in each case optionally nitro-, cyano-, carboxyl-, carbamoyl-, thiocarbamoyl-, sulfo-, chlorosulfonyl-, aminosulfonyl-, halogen-, $C_1$–$C_4$-alkyl-, $C_1$–$C_4$-halogenoalkyl-, $C_1$–$C_4$-alkoxy-, $C_1$–$C_4$halogenoalkoxy-, $C_1$–$C_4$-alkylthio-, $C_1$–$C_4$-halogenoalkylthio-, $C_1$–$C_4$alkylsulfonyl-, $C_1$–$C_4$-halogenoalkylsulfinyl-, $C_1$–$C_4$-alkylsulfonyl-, $C_1$–$C_4$-halogenoalkylsulfonyl- or $C_1$–$C_4$-alkoxy-carbonyl-substituted phenyl, naphthyl or heterocyclyl selected from the group consisting of furyl, tetrahydrofuryl, benzofuryl, dihydrobenzofuryl, dioxolanyl, dioxanyl, benzodioxanyl, pyrrolyl, pyrazolyl, imidazolyl, benzimidazolyl, triazolyl, oxazolyl, isoxazolyl, benzoxazolyl, thiazolyl, isothiazolyl, benzothiazolyl, pyridinyl, quinolinyl, isoquinolinyl, pyrimidinyl, pyrazinyl, pyridazinyl, quinazolinyl, quinoxalinyl, and $R^7$ represents hydrogen, represents in each case optionally cyano-, halogen- or $C_1$–$C_4$-alkoxy-substituted alkyl, alkoxy, alkylthio, alkylamino or dialkylamino having in each case 1 to 6 carbon atoms in the alkyl groups, represents in each case optionally cyano- or halogen-substituted alkenyl or alkinyl having in each case 2 to 6 carbon atoms, represents in each case optionally cyano-, halogen- or $C_1$–$C_4$-alkyl-substituted cycloalkyl or cycloalkylalkyl having in each case 3 to 6 carbon atoms in the cycloalkyl groups and optionally 1 to 4 carbon atoms in the alkyl moiety, or represents in each case optionally nitro-, cyano-, carboxyl-, carbamoyl-, thiocarbamoyl-, sulfo-, chlorosulfonyl-, aminosulfonyl-, halogen-, $C_1$–$C_4$-alkyl-, $C_1$–$C_4$-halogenoalkyl-, $C_1$–$C_4$alkoxy-, $C_1$–$C_4$-halogenoalkoxy-, $C_1$–$C_4$-alkylthio-, $C_1$–$C_4$-halogenoalkylthio-, $C_1$–$C_4$-alkylsulfinyl-, $C_1$–$C_4$-halogenoalkylsulfinyl-, $C_1$–$C_4$alkylsulfonyl-, $C_1$–$C_4$-halogenoalkylsulfonyl- or $C_1$–$C_4$-alkoxy-carbonyl-substituted phenyl, naphthyl or heterocyclyl selected from the group consisting of furyl, tetrahydrofuryl, benzofuryl, dihydrobenzofuryl, benzodioxanyl, pyrrolyl, pyrazolyl, imidazolyl, benzimidazolyl, oxazolyl, isoxazolyl, benzoxazolyl, benzothiazolyl, pyridinyl, quinolinyl, isoquinolinyl, pyrimidinyl, pyrazinyl, pyridazinyl, quinazolinyl, quinoxalinyl.

3. A process for preparing a phenyluracil compound of the formula (I) according to claim 1 comprising the step of (a) reacting an amino-alkeneoic ester of formula (II)

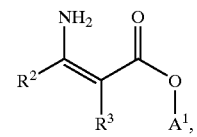

(II)

in which $R^2$ and $R^3$ are each as defined in claim 2 and $A^1$ represents alkyl, aryl or arylalkyl, with a phenyl urethane (phenyl carbamate) of formula (III)

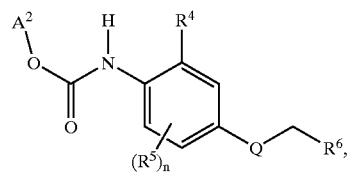

(III)

in which n, Q, $R^4$, $R^5$ and $R^6$ are each as defined in claim 2 and $A^2$ represents alkyl, aryl or arylalkyl, optionally in the presence of a reaction auxiliary selected from the group consisting of inorganic bases, organic bases, inorganic acid acceptors and organic acid acceptors, and optionally in the presence of a diluent.

4. A phenyluracil compound of the formula (Ia),

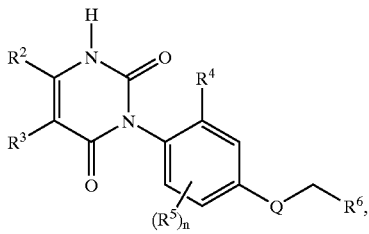

(Ia)

in which n, Q, $R^2$, $R^3$, $R^4$, $R^5$ and $R^6$ are each as defined in claim 1.

5. A phenyluracil compound of the formula (Ic),

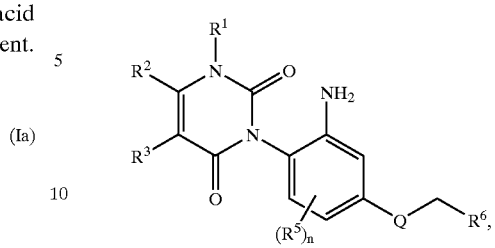

(Ic)

in which n, Q, $R^1$, $R^2$, $R^3$, $R^5$ and $R^6$ are each as defined in claim 1.

6. A herbicidal composition comprising one or more phenyluracil compound(s) according to claim 1, and an extender and/or a surfactant.

7. A method of controlling undesirable plants comprising the step of applying an effective amount of one or more phenyluracil compound(s) according to claim 1 to a member selected from said plants, a habitat of said plants and combinations thereof.

* * * * *